(12) United States Patent
Zhang et al.

(10) Patent No.: US 9,656,311 B2
(45) Date of Patent: May 23, 2017

(54) DITHIOCARBAMATE FUNCTIONALIZED DENDRIMER WITH ALKYLENEDIAMINE CORE AS SOIL HEAVY METAL IMMOBILIZATION AMENDMENT AND PREPARATION METHOD THEREOF

(71) Applicant: Tongji University, Shanghai (CN)

(72) Inventors: Bingru Zhang, Shanghai (CN); Fengting Li, Shanghai (CN); Huangpu Zhao, Shanghai (CN); Weixiao Zhou, Shanghai (CN); Haiyan Tian, Shanghai (CN)

(73) Assignee: Tongji University, Shanghai (CN)

( * ) Notice: Subject to any disclaimer, the term of this patent is extended or adjusted under 35 U.S.C. 154(b) by 41 days.

(21) Appl. No.: 14/737,495

(22) Filed: Jun. 12, 2015

(65) Prior Publication Data
US 2016/0237029 A1 Aug. 18, 2016

(30) Foreign Application Priority Data
Feb. 12, 2015 (CN) .......................... 2015 1 0072596

(51) Int. Cl.
*A62D 3/33* (2007.01)
*B09C 1/08* (2006.01)
*C07C 333/26* (2006.01)

(52) U.S. Cl.
CPC .............. *B09C 1/08* (2013.01); *C07C 333/26* (2013.01); *B09C 2101/00* (2013.01)

(58) Field of Classification Search
CPC ... C07C 333/16; C07C 213/06; C07C 213/08; C07C 227/06; C07C 333/20; B09C 1/08; B09C 2101/00; A62D 3/33; A62D 2101/08
USPC ......................................................... 588/315
See application file for complete search history.

(56) References Cited

U.S. PATENT DOCUMENTS

2015/0283417 A1* 10/2015 Zhang ..................... A62D 3/33
588/315

* cited by examiner

*Primary Examiner* — Shane Fang

(57) ABSTRACT

A dithiocarbamate functionalized dendrimer with an alkylenediamine core, a dithiocarbamate pendant functional group and a dithiocarbamate end functional group, as a soil heavy metal immobilization amendment, and a preparation method thereof are provided. The dithiocarbamate functionalized dendrimer has a chemical formula of $(CH_2)_a\{N[CH_2CH_2COOCH_2C(C_2H_5)(CH_2OCOCH_2CH_2N(CSSM) CH_2(CH_2)_bCH_2N(CSS\ M)_2)_2]_2\}_2$, wherein a is a positive integer larger than 2; b is a positive integer at a range of 0-4; and M is $Na^+$, $NH_4^+$ or $K^+$. The dithiocarbamate functionalized dendrimer with the alkylenediamine core is used for an in-suit immobilization remediation for soil contaminated by heavy metals, and has advantages of a small dosage, high efficiency, safety and rapidness. The dendrimer is able to effectively immobilize exchangeable and carbonated bound forms of the heavy metals, in such a manner that the immobilized heavy metals are able to resist an influence from natural environment for a long term, such as an acid rain.

1 Claim, No Drawings

DITHIOCARBAMATE FUNCTIONALIZED DENDRIMER WITH ALKYLENEDIAMINE CORE AS SOIL HEAVY METAL IMMOBILIZATION AMENDMENT AND PREPARATION METHOD THEREOF

CROSS REFERENCE OF RELATED APPLICATION

The present invention claims priority under 35 U.S.C. 119(a-d) to CN 201510072596.0, filed Feb. 12, 2015.

BACKGROUND OF THE PRESENT INVENTION

1. Field of Invention

The present invention relates to a technical field of environmental protection, especially belongs to a technical field of soil contamination treatment, and more particularly to a dithiocarbamate functionalized dendrimer with an alkylenediamine core as a soil heavy metal immobilization amendment and a preparation method thereof.

2. Description of Related Arts

Along with the continuous expansion of the industrial production scale and the rapid development of the urbanization in China, the soil is suffering from various degrees of heavy metal contaminations. The soil heavy metal contamination mainly comes from the human activities, such as mining, smelting, electroplating, tanning and metal processing.

The *Report on the national general survey of soil contamination*, firstly published on Apr. 17, 2014, by the Ministry of Environmental Protection and the Ministry of Land and Resources of the People's Republic of China, indicates that 16.1% of the surveyed land of 6.3 million square kilometers (about 65.6% of the territorial area, covering all the arable land and part of the forest land, the grassland and the construction land of China) is contaminated, wherein 82.8% of the contaminated land is contaminated by the heavy metals; and 19.4% of the arable land is contaminated, mainly by the pollutants of cadmium (Cd), nickel, copper, arsenic, mercury and plumbum (Pb), which means that nearly one fifth of the arable land suffers from the heavy metal contamination. In China, the soil heavy metal contamination leads to a decrease of 10 million tons in the food production, and 12 million tons of food is contaminated by the heavy metals.

Unlike the organic pollutants, the non-degradable heavy metals are unable to be remedied through a microbial degradation or a chemical degradation. Thus, the soil heavy metal contamination is accumulative and relatively stable, which leads to a relatively difficult remediation of the soil contaminated by the heavy metals.

Generally, the soil heavy metal remediation is divided into the physical remediation, the bio-remediation and the chemical remediation.

The physical remediation mainly comprises: agricultural engineering measures (soil replacement and soil dressing), heat treatment, vitrification and electrokinetic remediation. The agricultural engineering measures are suitable for the small area of the contaminated soil. However, because of involving digging and moving soil, the agricultural engineering measures consume massive manpower, material resources and financial resources; and the replaced soil also needs to be treated. Thus, the agricultural engineering measures have a high treatment cost; it is difficult to treat a deep pollution by the agricultural engineering measures, especially for a situation that the pollutants permeate into the saturated layer soil and the underground water; and the agricultural engineering measures destroy the original soil structure and the ecological environment. The heat treatment has a high energy consumption and a high operation cost, and is merely suitable for volatile pollutants. The vitrification is expensive. The vitrified soil still needs to be landfilled, which occupies lands and wastes resources. The electrokinetic remediation is merely suitable for the sandy soil and expensive.

The bio-remediation, through the metabolism of the organisms (microorganisms, plants and animals), absorbs and removes the heavy metals in the soil or transforms the heavy metals, so as to reduce the toxicity and purify the soil. The microorganism remediation is an emerging soil remediation method, but still in the research phase because of a high cost and a difficult microbial strain selection. The lower animals for remediating the soil are limited in the number, and the lower animals after absorbing the heavy metals may be released into the soil again to cause a secondary pollution. The phytoremediation accumulates the heavy metals in the soil by accumulators and hyperaccumulators, and the plants are collected and centralized to detach the heavy metals from the contaminated soil, so as to remove the heavy metals in the contaminated soil. The phytoremediation is the most promising original ecological soil treatment technology at present, but is obviously disadvantageous as follows. Firstly, the hyperaccumulators grow slowly and have a long remediation period, generally 3-5 years; secondly, the phytoremediation is merely able to accumulate one specific heavy metal or some specific heavy metals, but the soil is generally contaminated by a combination of the heavy metals; thirdly, the soil rich in the heavy metals impairs the growth of the hyperaccumulators, leading to the low heights, the low biomass, the slow growth and the long growth period of the hyperaccumulators, so as to decrease the remediation efficiency and the remediation rate; and fourthly, the hyperaccumulators need to be harvested and properly disposed as waste, otherwise may threaten the biodiversity to a certain degree.

The chemical remediation comprises chemical washing remediation and in-situ chemical immobilization remediation.

The chemical washing remediation washes the soil with washing agents (surfactants, organic acids and salts thereof, and chelating agents) to transfer the heavy metals from the soil to the waste water, and then the waste water is recycled and treated, so as to remedy the soil. However, the chemical washing remediation is expensive; while removing the heavy metals, the chemical washing remediation leads to a nutrient loss of the soil, and carries the washing agents into the soil, becoming another contamination resource. The chemical washing remediation destroys the soil structure, contaminates the underground water, and leads to a high environmental risk.

The in-situ chemical immobilization remediation is to add chemical reagents or chemical materials into the soil. Through absorption, precipitation, complexing, ion exchanging and a redox reaction, the heavy metals are turned into insoluble substances having a low solubility and a low dissolution rate, which reduces the mobility of the heavy metals in the soil and the possibility to be absorbed by the plants. Thus, usually the chemical materials are also called amendments. The heavy metals are immobilized stably in the soil through the amendments, so as to realize treating and remediating the contaminated soil.

Compared with other remediation measures, the in-situ chemical immobilization remediation of the soil with the amendments has advantages of the wide application scope, the high processing capacity, the fast yield, being economical and convenient, and maintaining the inherent physical and chemical properties of the soil unchanged. The in-situ chemical immobilization remediation is considered as a potential alternative technology which is able to reduce the health risk of the heavy metal environment, and thus has a good application prospect.

The conventional amendments are mainly divided into the inorganic amendments and the organic amendments. The inorganic amendments mainly comprise minerals (sepiolite, bentonite, montmorillonoid, zeolite powder, attapulgite, diatomite and metallic oxide ores such as aluminum oxide ore, manganese oxide ore and iron oxide ore), phosphates (phosphate, hydrophosphate and sodium dihydrogen phosphate), alkaline substances (calcium oxide, calcium hydroxide, carbonate and bicarbonate), sulfides (polysulfide, hydrosulfide salt and sulfide) and biochars (straw charcoal powder, rice husk charcoal powder and bamboo shell charcoal powder). The organic amendments comprise humic acids, organic fertilizers and chelating agents.

The published amendment is usually one of the conventional amendments or a combination of at least two of the conventional amendments. The Chinese patent application, CN 200910070713.4, discloses a combined amendment comprising sepiolite and dicalcium phosphate, which is able to immobilize the soil having a total Cd content of 1.2 mg/Kg and an available Cd content of 0.6 mg/Kg. When the addition dosage of the combined amendment reaches 9% of the soil, the available Cd content is decreased to 0.23 mg/Kg by 61%. The Chinese patent application, CN 201210227669.5, discloses a combined amendment comprising slaked lime, monopotassium phosphate, plant ash and silkworm excrement, for immobilizing and remedying the soil containing Pb and Cd. When the addition dosage of the combined amendment reaches 2% of the soil, the available Pb content is decreased by 47.61% and the available Cd content is decreased by 50.57% after 30 days. The Chinese patent application, CN 201110203080.7, discloses a combined amendment comprising calcium hydroxide, fly ash, sodium carbonate, polycrylamide and sodium sulfate, for processing the soil with an in-situ immobilization remediation. When the addition dosage of the combined amendment reaches 5% of the soil, the leaching content of Pb, Zinc (Zn), Cd and Copper (Cu) is respectively decreased from 2.86 mg/L, 1.37 mg/L, 0.31 mg/L and 4.65 mg/L to 0.35 mg/L, 0.42 mg/L, 0.03 mg/L, 0.42 mg/L and 0.84 mg/L. The Chinese patent application discloses a combined amendment comprising humic acid mineral powder, calcium magnesium phosphate fertilizer and quicklime. When the addition dosage of the combined amendment reaches 3% of the soil, the available Cd content in the soil is decreased from 8.90 mg/Kg to 7.38 mg/Kg. The Chinese patent application, CN 201210244674.7, discloses a combined amendment comprising rice husk charcoal, powdered straw and sifted fly ash. When the addition dosage of the combined amendment reaches 8% of the soil, the available Pb content in the soil is decreased by 73.25%.

The above conventional amendments have the following limitations. Firstly, for the heavily contaminated soil, the immobilization effect of the conventional amendments is negligible. Secondly, the conventional amendments are unable to guarantee a long-term and stable existence of the remedied soil in the nature. When the environment changes, the immobilized heavy metals may be activated and then be dissolved out again, causing a secondary contamination.

Thus, it is urgent to provide a highly-efficient amendment with an enhanced ability to stabilize the heavy metals with regard to the research of the in-situ remediation amendment of the heavy metals in the soil.

With the development of the polymers, based on the conventional one-dimensional linear, two-dimensional crosslinked or slightly branched polymers, the highly-branched polymers having a three-dimensional spatial structure are developed. According to the structure, the highly-branched polymers are divided into the dendrimers and the hyperbranched polymers. The dendrimers have a regular structure, but the hyperbranched polymers have an irregular structure. In the 21$^{st}$ century, the highly-branched polymer has attracted more and more attentions of the scientists around the world, because of the special structure. The highly-branched polymer has an important application prospect in the fields of industry, agriculture, national defense, biomedical, sustained-release materials and catalysis.

The present invention adopts a dithiocarbamate functionalized dendrimer with an alkylenediamine core as a soil heavy metal immobilization amendment, which has good performance in stabilizing the heavy metals in the soil, has an ability to reduce the available heavy metals and the carbonate bound forms of the heavy metals and to well resist acid rain, and guarantees a long-term stability of the remedied soil in the environment.

SUMMARY OF THE PRESENT INVENTION

An object of the present invention is to overcome the large dosage and the poor stabilization of the conventional immobilization amendments, and to provide a dithiocarbamate functionalized dendrimer with an alkylenediamine core as a soil heavy metal immobilization amendment and a preparation method thereof. The soil heavy metal immobilization amendment of the present invention has good stabilization performance for heavy metals in soil and a strong resistance to acid and alkali, and satisfies a long-term safety requirement of the soil.

Accordingly, in order to accomplish the above objects, the present invention provides a soil heavy metal immobilization amendment which is a dithiocarbamate functionalized dendrimer with an alkylenediamine core.

The dithiocarbamate functionalized dendrimer with the alkylenediamine core has a chemical formula of:

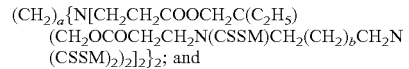

and the dithiocarbamate functionalized dendrimer with the alkylenediamine core has a structural formula of:

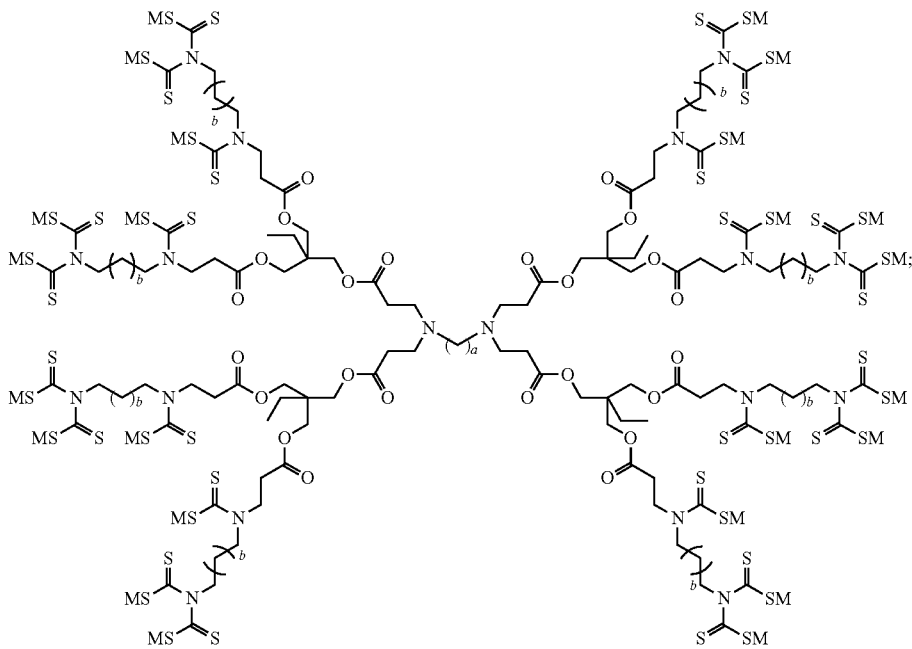

wherein a is a positive integer larger than 2; b is a positive integer at a range of 0-4; and M is $Na^+$, $NH4^+$ or $K^+$.

The present invention also provides a method for preparing the dithiocarbamate functionalized dendrimer with the alkylenediamine core as the soil heavy metal immobilization amendment, comprising steps of:

(1) Preparing a double bond-terminated lower generation dendrimer, comprising steps of:

Adding a methanol solution of trimethylolpropane triacrylate ($C_2H_5C(CH_2OOCHC=CH_2)_3$, TMPTA for short) into a first round-bottom flask with a first stirrer, a first reflux condenser and a first thermometer; then dropping a methanol solution of first alkylenediamine ($H_2N(CH_2)_aNH_2$, ADA for short) by two to five times into the first round-bottom flask, at a temperature of lower than 10° C., under a nitrogen protection and a stirring condition, wherein a is a positive integer larger than 2; controlling a dropping speed to keep the temperature lower than 10° C. when dropping; reacting for 8-16 h at a temperature of 25° C. after each dropping; reacting for 12-18 h at the temperature of 25° C. after all the first ADA is dropped; filtering a pale amber product which is dissolved out after reacting; washing the pale amber product with methanol; drying in a vacuum at a temperature of 40° C.; and obtaining a pale amber double bond-terminated lower generation dendrimer (ADA/TMPTA for short);

wherein the ADA/TMPTA has a chemical formula of:

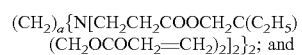

and a reaction equation of the step (1) is:

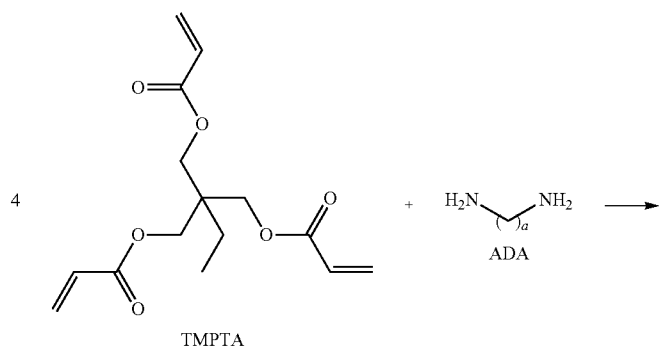

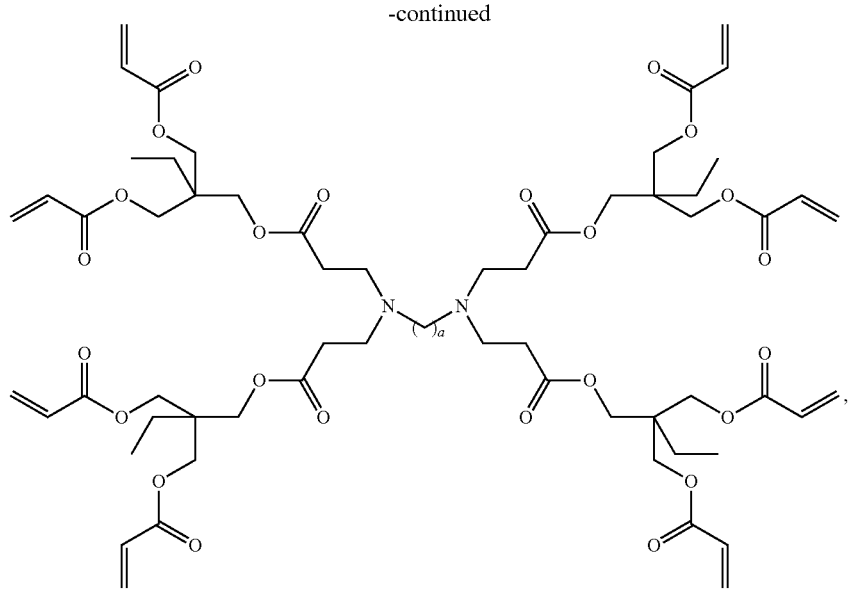

ADA/TMPTA wherein a is the positive integer larger than 2;

(2) Preparing an amine-terminated higher generation dendrimer, comprising steps of:

Adding an alcohol solution of second alkylenediamine ($H_2NCH_2(CH_2)_bCH_2NH_2$, ADA for short) into a second round-bottom flask with a second stirrer, a second reflux condenser and a second thermometer, wherein b is a positive integer at a range of 0-4; adding the ADA/TMPTA obtained by the step (1) to the second round-bottom flask, and then stirring and uniformly mixing, at the temperature of lower than 10° C., under the nitrogen protection and the stirring condition; reacting for 20-30 h at the temperature of 25° C.; distilling under a reduced pressure for 3-5 h at a temperature of 80-100° C. to remove the methanol and redundant ethylenediamine (EDA for short); and obtaining a pale amber viscous product which is the amine-terminated higher generation dendrimer (ADA/TMPTA/ADA for short);

wherein the ADA/TMPTA/ADA has a chemical formula of:

$(CH_2)_a\{N[CH_2CH_2COOCH_2C(C_2H_5)\allowbreak(CH_2OCOCH_2CH_2NHCH_2(CH_2)_bCH_2NH_2)_2]_2\}_2$; and a reaction equation of the step (2) is:

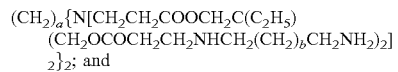

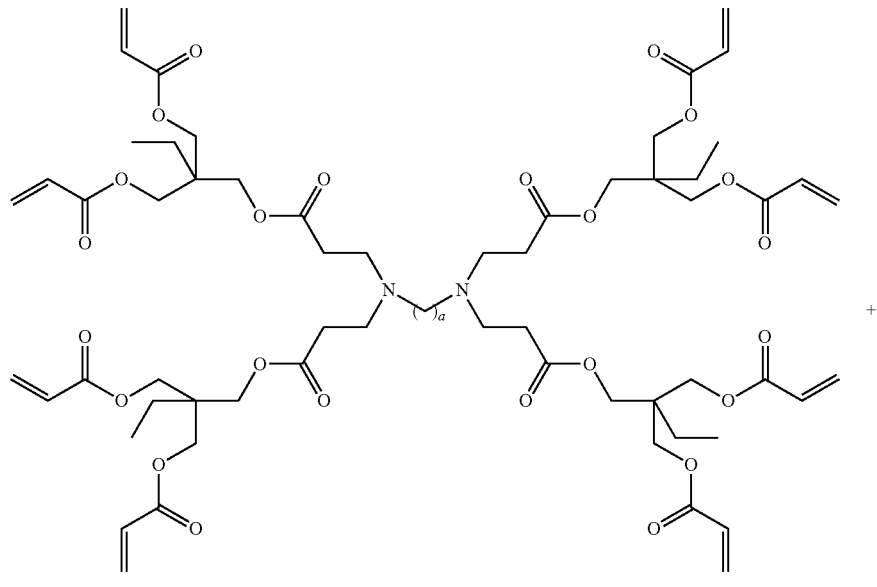

ADA/TMPTA

8  $H_2N\underset{b}{\frown}NH_2$
ADA →

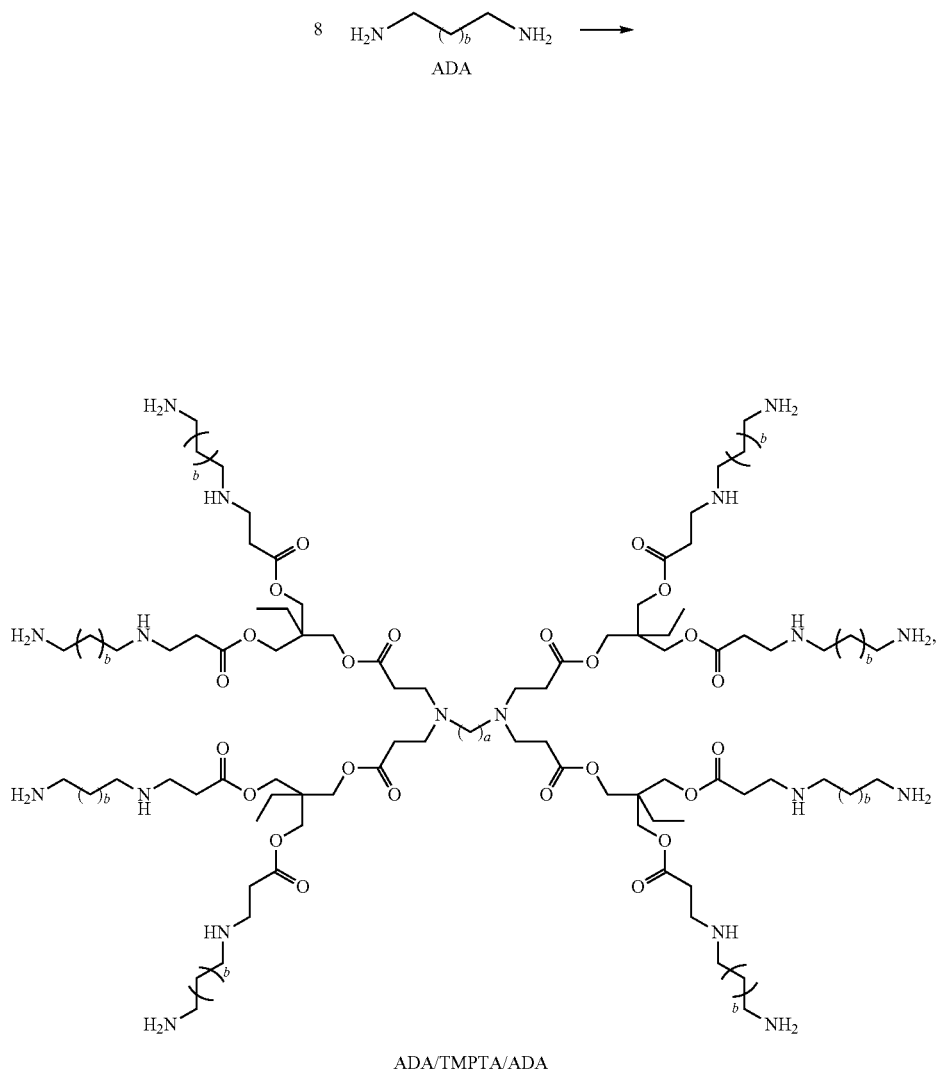

ADA/TMPTA/ADA wherein a is the positive integer larger than 2 and b is the positive integer at the range of 0-4; and (3) Preparing a dithiocarbamate functionalized dendrimer with an alkylenediamine core, comprising steps of:

Adding an alcohol solution of the ADA/TMPTA/ADA obtained by the step (2) into a third round-bottom flask with a third stirrer, a third reflux condenser and a third thermometer; decreasing the temperature to be lower than 10° C., and introducing nitrogen; dropping an alkali solution slowly into the third round-bottom flask at the temperature of lower than 10° C., and then dropping an ethanol solution of carbon disulfide at the temperature of lower than 10° C., so as to form an aqueous reaction mixture; reacting, by the aqueous reaction mixture, for 2-5 h at a temperature of 5-10° C. after dropping; increasing the temperature to 25° C., and then continuing reacting, by the aqueous reaction mixture, for 3-5 h; storing the aqueous reaction mixture overnight to dissolve out white precipitate; filtering out the precipitate and washing the precipitate with a small amount of ethanol; and then filtering again to obtain a target product: the dithiocarbamate functionalized dendrimer with the alkylenediamine core (ADA/TMPTA/ADA-24CSSNa for short);

wherein the ADA/TMPTA/ADA-24CSSNa has a chemical formula of:

a reaction equation of the step (3) is:

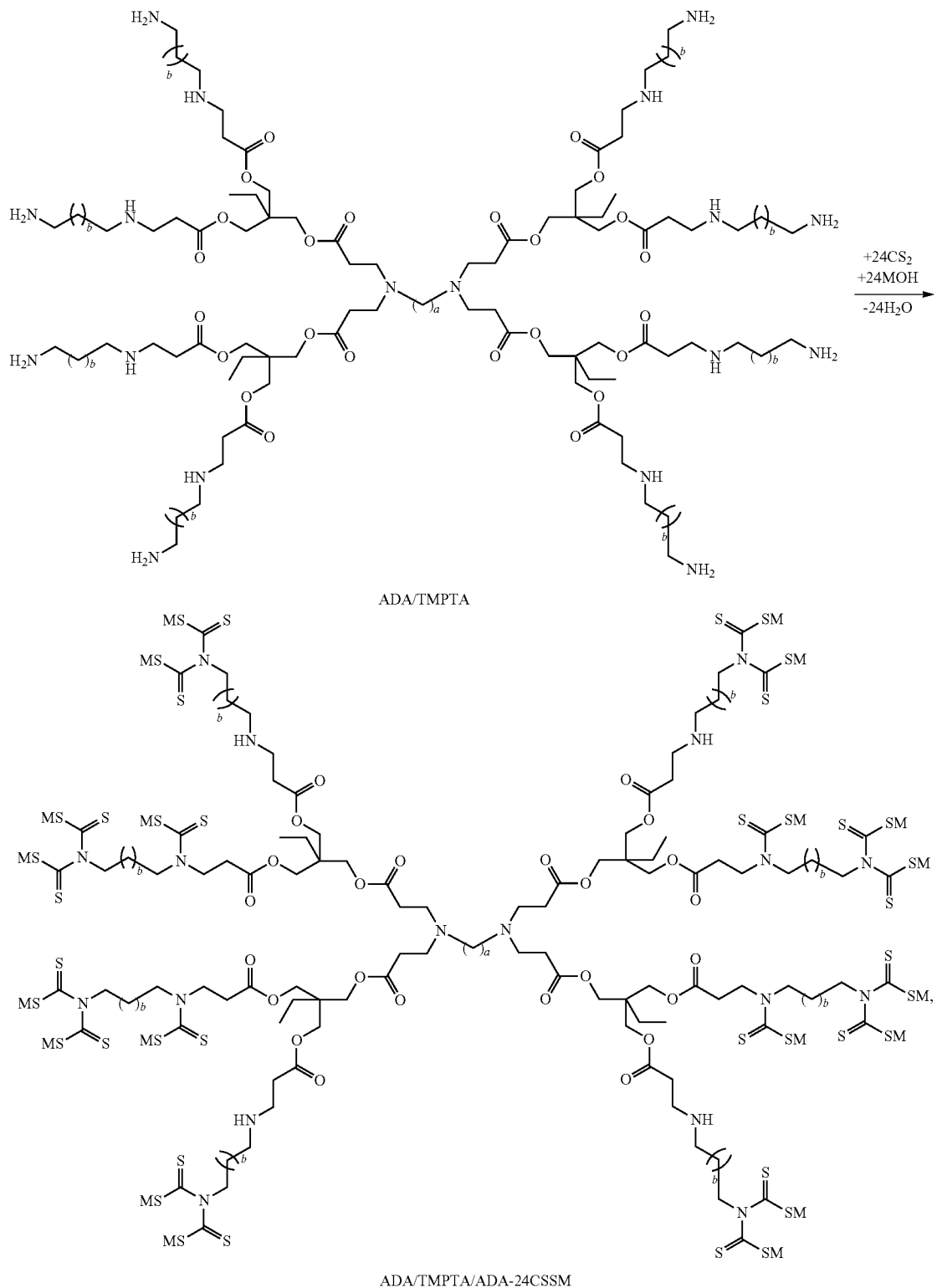

ADA/TMPTA

ADA/TMPTA/ADA-24CSSM wherein a is the positive integer larger than 2, b is the positive integer at the range of 0-4, and M is $Na^+$, $NH_4^+$ or $K^+$.

In the step (1), a mole ratio of the TMPTA to the first ADA is 4.1:1-4.9:1; in the step (2), a mole ratio of the ADA/TMPTA to the second ADA is 1:15-1:20; and in the step (3), a mole ratio among the ADA/TMPTA/ADA, the carbon disulfide and the alkali is 1:(30-36):(30-36).

According to the present invention, the TMPTA, the ADA and the carbon disulfide are all commercially available.

According to the present invention, the alkali is sodium hydroxide, potassium hydroxide or ammonia, wherein the sodium hydroxide, the potassium hydroxide and the ammonia are all commercially available.

During the research, inventors of the present invention find that: when the TMPTA and the first ADA are mixed according to the mole ratio of 4.1:1-4.9:1, it is possible to theoretically obtain a double bond-terminated polymer with the alkylenediamine core; however, an adding order and an adding method of the raw materials determine a purity and a yield of the product. For example, Chunhua Ning prepared a double bond-terminated lower generation dendrimer, wherein a and b were both 2 (*Dendrimer synthesis with raw materials of EDA and TMPTA*, $1^{st}$ series of Engineering Technology of China Doctor/Master Dissertations Full-text Database, $2^{nd}$ issue in 2004, B014-14, p 18). The method of Chunhua Ning included steps of: respectively adding the methanol, the TMPTA and the EDA into a three-necked bottle; and stirring for 6-28 h at a temperature of 30-40° C. However, when a mole ratio of the TMPTA to the EDA was 4.71:1, 4.44:1 and 4:1, and when the reaction time was respectively 3.5 h, 2.5 h and 0.5 h, the aqueous reaction mixture was solidified and failed to continue reacting. When the mole ratio of the TMPTA to the EDA was 5.33:1-8.00:1, it is failed to obtain a product. The conclusion was drawn from the thesis of Chunhua Ning that a product having an ideal purity is merely obtained at a temperature of 30° C. when the mole ratio of the TMPTA to the EDA is 5.00:1 and the reaction time is 6 h, wherein the yield was 65.11%.

During the research, the inventors of the present invention also find that: when the TMPTA and the EDA is simultaneously added according to a stoichiometric ratio of 4:1, the aqueous reaction mixture is solidified in merely half an hour; and, when the mole ratio of the EDA to the TMPTA increases from 1:4.0 to 1:4.9, a time to solidify gradually increases. The reason is that excessive TMPTA prevents other two double bonds of the same TMPTA from reacting with a primary amine group of the EDA molecule, which avoids a chain reaction to form a bridge structure and accordingly avoids the aqueous reaction mixture being solidified. When the mole ratio of the EDA to the TMPTA is 1:6.0, although the aqueous reaction mixture is not solidified, a product yield is low. The inventors of the present invention find that: when the adding order is changed to firstly add the TMPTA and then add the EDA by several times, since the TMPTA is excessive all the time, it is guaranteed that the TMPTA react with the EDA according to the mole ratio of 4:1, so as to prevent the other double bond of the TMPTA from reacting with other EDA to form the bridge structure and accordingly avoid the aqueous reaction mixture being solidified. When the TMPTA and the EDA is added according to the stoichiometric ratio of 4:1, the product yield is 79.91%. When the mole ratio of the TMPTA to the EDA increases from 4.1:1 to 4.9:1, the product yield gradually increases; when the mole ratio of the TMPTA to the EDA increases from 5.0:1 to 5.4:1, the product yield gradually decreases; and, when the mole ratio of the TMPTA to the EDA is larger than 5.5:1, it is failed to obtain the product with a normal processing method. The reason is that the product is insoluble in the methanol, but soluble in the TMPTA, and thus the product is unable to dissolve out from a mixed liquid of the excessive TMPTA and the methanol. Thus, the mole ratio of the TMPTA to the EDA is preferably lower than 5.0:1, namely the mole ratio of the TMPTA to the ADA is 4.1:1 to 4.9:1. The inventors of the present invention further find in the research that: when the first ADA ($H_2N(CH_2)_aNH_2$, a>2), such as propanediamine and butanediamine, serves as the core, a yield of accordingly obtained double bond-terminated lower generation dendrimer is higher than the yield of obtained double bond-terminated lower generation dendrimer with an ethylenediamine core, because of avoiding a steric hindrance of a reaction between four TMPTA molecules and an ADA molecule. The inventors of the present invention further find that: with an increase of a reaction temperature, an appearance color of the product is deepened and the product yield is slightly decreased. The reason may be that the increase of the reaction temperature leads to an oxidation of the amine group and accordingly a decrease in purity. Thus, preferably, the reaction temperature is 25° C.

In the steps of preparing the double bond-terminated lower generation dendrimer of the present invention, the first ADA ($H_2N(CH_2)_aNH_2$, a>2) serves as the core; the TMPTA is firstly added and then the first ADA is added by several times; and the mole ratio of the TMPTA to the first ADA is 4.1:1-4.9:1.

The present invention further provides a method for in-suit immobilizing and remedying soil contaminated by heavy metals, comprising steps of: preparing the dithiocarbamate functionalized dendrimer with the alkylenediamine core into a solution; uniformly mixing the solution with the soil contaminated by the heavy metals, wherein an addition dosage of the solution is 0.5%-5% of a weight of the soil; and storing the mixed soil for at least one day, so as to realize a quick in-situ immobilization for the soil contaminated by the heavy metals, and to resist an influence from natural environment for a long term (such as acid rain).

The dendrimer provided by the present invention is a functionalized dendrimer with the alkylenediamine core, a dithiocarbamate pendant functional group and a dithiocarbamate end functional group. According to experiments, the dithiocarbamate functionalized dendrimer with the alkylenediamine core is able to effectively immobilize the heavy metals in the soil, because of a special highly-branched structure thereof. Compared with the conventional immobilization amendments in the market, the dithiocarbamate functionalized dendrimer with the alkylenediamine core of the present invention has a low addition dosage and a good resistance to acid rain while immobilizing the heavy metals, and guarantees a long-term safety of the remedied soil.

The dithiocarbamate functionalized dendrimer with the alkylenediamine core, provided by the present invention, is able to serve as the in-suit immobilization amendment for the soil contaminated by the heavy metals, and is also applicable to stabilize the heavy metals in fly ashes of waste incineration and treat waste water containing the heavy metals.

These and other objectives, features, and advantages of the present invention will become apparent from the following detailed description, the accompanying drawings, and the appended claims.

DETAILED DESCRIPTION OF THE PREFERRED EMBODIMENT

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

Stabilizers as comparisons 1-2 are both commercially available.

Comparison 1: inorganic stabilizer, sodium sulfide ($Na_2S$)

Comparison 2: organic stabilizer, thiourea ($H_2NCSNH_2$)

EXAMPLE 1

Preparation of Dithiocarbamate Functionalized Dendrimer with Butanediamine Core (a=4, b=2)

(1) Preparation of Double Bond-Terminated Lower Generation Dendrimer 266.40 g (50.00%, 0.45 mol) of a methanol solution of trimethylolpropane triacrylate (TMPTA for short) was added into a first round-bottom flask with a first stirrer, a first reflux condenser and a first thermometer. 8.80 g (50.00%, 0.05 mol) of a methanol solution of butanediamine (1,4-Butanediamine, BDA for short) was dropped into the first round-bottom flask to form a first mixture at a temperature of lower than 10° C., under a nitrogen protection and a stirring condition, wherein a dropping speed was controlled to keep the temperature lower than 10° C. when dropping. The temperature was increased to 25° C.; then, the first mixture reacted for 10 h. Thereafter, the temperature was decreased to 10° C., and 8.80 g (50.00%, 0.05 mol) of the methanol solution of BDA was added again into the first round-bottom flask to form a second mixture, wherein the dropping speed was controlled to keep the temperature lower than 10° C. when dropping. Thereafter, the temperature was increased to 25° C. and the second mixture reacted for 16 h. After the reaction was finished, a first pale amber viscous product was dissolved out. The first pale amber viscous product was filtered out, washed with ethanol, and dried in a vacuum at a temperature of 40° C. Then, a pale amber product of 120.86 g was obtained, namely a double bond-terminated lower generation dendrimer (BDA/TMPTA for short) with a yield of 95.02%.

(2) Preparation of Amine-Terminated Higher Generation Dendrimer 96.00 g (50.00%, 0.80 mol) of an ethanol solution of ethylenediamine (EDA for short) was added into a second round-bottom flask with a second stirrer, a second reflux condenser and a second thermometer. 127.20 g (50.00%, 0.05 mol) BDA/TMPTA obtained by the step (1) was added into the second round-bottom flask to form a third mixture at the temperature of lower than 10° C. under the nitrogen protection and the stirring condition, stirred and uniformly mixed. Thereafter, the third mixture reacted for 24 h at the temperature of 25° C. Then, the third mixture was distilled under a reduced pressure for 5 h at a temperature of 85° C. to remove ethanol and excessive EDA, so as to obtain a second pale amber viscous product of 86.05 g, namely an amine-terminated higher generation dendrimer (BDA/TMPTA/EDA) with a yield of 98.23%.

(3) Preparation of Dithiocarbamate Functionalized Dendrimer with Butanediamine Core 87.60 g (50.00%, 0.025 mol) of an ethanol solution of the BDA/TMPTA/EDA obtained by the step (2) was added into a third round-bottom flask with a third stirrer, a third reflux condenser and a third thermometer. The temperature was decreased to be lower than 10° C. and nitrogen was introduced. At the temperature of lower than 10° C., 60.00 g (50.00%, 0.75 mol) of a sodium hydroxide solution was slowly dropped to the third round-bottom flask, and then 121.60 g (50.00%, 0.80 mol) of an ethanol solution of carbon disulfide was dropped to the third round-bottom flask, so as to form a fourth mixture, wherein the temperature was controlled to be lower than 10° C. when dropping. After dropping is finished, the fourth mixture reacted for 4 h at the temperature of 10° C. Thereafter, the temperature was increased to 25° C. and the fourth mixture continued to react for 5 h. The fourth mixture, as an aqueous reaction mixture, was stored overnight to dissolve out white precipitate. The white precipitate was filtered out, washed with a small amount of the ethanol, and then filtered out again. Thereafter, a product of 96.65 g was obtained, namely a dithiocarbamate functionalized dendrimer with a butanediamine core (BDA/TMPTA/EDA-24CSSNa) with a yield of 94.20%.

A nuclear magnetic resonance $^{13}$C NMR (D$_2$O) spectrum of the obtained star-shaped hyperbranched polymer is: 8.56 ppm, 21.25 ppm, 27.16 ppm, 32.37 ppm, 33.65 ppm, 36.15 ppm, 48.26 ppm, 49.92 ppm, 50.36 ppm, 54.26 ppm, 55.39 ppm, 65.87 ppm, 66.21 ppm, 176.68 ppm, 177.11 ppm, 207.24 ppm and 210.15 ppm. A structure of the BDA/TMPTA/EDA-24CSSNa is:

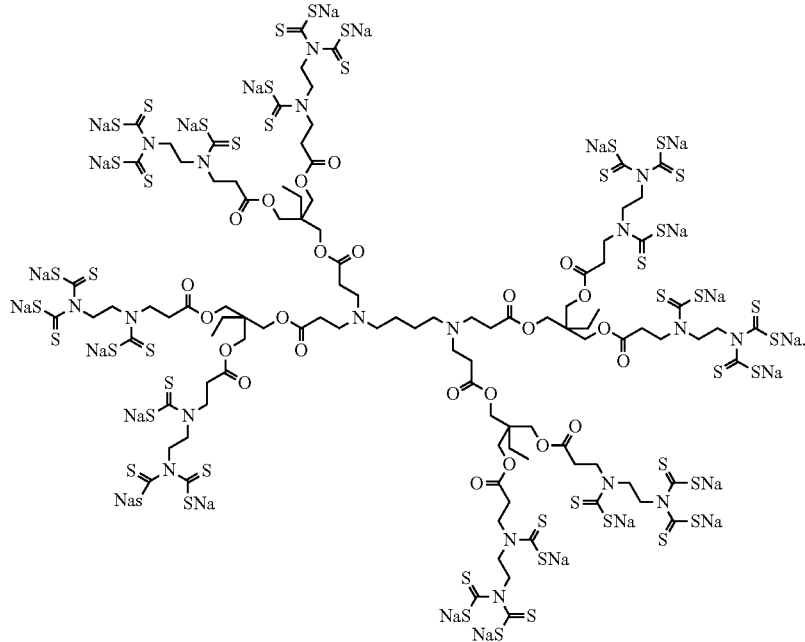

EXAMPLE 2

Preparation of Dithiocarbamate Functionalized Dendrimer with Hexanediamine Core (a=6, b=4)

(1) Preparation of Double Bond-Terminated Lower Generation Dendrimer 266.40 g (50.00%, 0.45 mol) of a methanol solution of trimethylolpropane triacrylate (TMPTA for short) was added into a first round-bottom flask with a first stirrer, a first reflux condenser and a first thermometer. 11.60 g (50.00%, 0.05 mol) of a methanol solution of hexanediamine (1,6-Hexanediamine, HDA for short) was dropped into the first round-bottom flask to form a first mixture, at a temperature of lower than 10° C., under a nitrogen protection and a stirring condition, wherein a dropping speed was controlled to keep the temperature lower than 10° C. when dropping. The temperature was increased to 25° C. and the first mixture reacted for 10 h. Thereafter, the temperature was decreased to 10° C., and 11.60 g (50.00%, 0.05 mol) of the methanol solution of HDA was dropped into the first round-bottom flask to form a second mixture, wherein the dropping speed was controlled to keep the temperature lower than 10° C. when dropping. Thereafter, the temperature was increased to 25° C. and the second mixture reacted for 16 h. After the reaction of the second mixture was finished, a first pale amber viscous product was dissolved out. The first pale amber viscous product was filtered out, washed with methanol, and dried in a vacuum at a temperature of 40° C., so as to obtain a pale amber product of 122.85 g, namely a double bond-terminated lower generation dendrimer (HDA/TMPTA for short) with a yield of 94.50%.

(2) Preparation of Amine-Terminated Higher Generation Dendrimer 140.80 g (50.00%, 0.80 mol) of a methanol solution of butanediamine (BDA for short) was added into a second round-bottom flask with a second stirrer, a second reflux condenser and a second thermometer. 130.00 g (50.00%, 0.05 mol) HDA/TMPTA obtained by the step (1) was added into the second round-bottom flask to form a third mixture, at the temperature of lower than 10° C., under the nitrogen protection and the stirring condition. After being stirred and uniformly mixed, the third mixture reacted for 24 h at the temperature of 25° C. Then, the third mixture was distilled under a reduced pressure for 5 h at a temperature of 95° C. to remove methanol and excessive BDA, so as to obtain a second pale amber viscous product of 98.21 g, namely an amine-terminated higher generation dendrimer (HDA/TMPTA/BDA) with a yield of 98.01%.

(3) Preparation of Dithiocarbamate Functionalized Dendrimer with Hexanediamine Core 100.20 g (50.00%, 0.025 mol) of a methanol solution of HDA/TMPTA/BDA obtained by the step (2) was added into a third round-bottom flask with a third stirrer, a third reflux condenser and a third thermometer. The temperature was decreased to be lower than 10° C. and nitrogen was introduced. At the temperature of lower than 10° C., 64.00 g (50.00%, 0.80 mol) of a sodium hydroxide solution was slowly dropped into the third round-bottom flask, and then 121.60 g (50.00%, 0.80 mol) of an ethanol solution of carbon disulfide was dropped into the third round-bottom flask, so as to form a fourth mixture, wherein the temperature was controlled to be lower than 10° C. when dropping. After dropping is finished, the fourth mixture reacted for 4 h at the temperature of 8° C. Then the temperature was increased to 25° C. and the fourth mixture continued to react for 5 h. Then, the fourth mixture, as an aqueous reaction mixture, was stored overnight to dissolve out white precipitate. The white precipitate was filtered out, washed with a small amount of ethanol, and then filtered again, so as to obtain a product of 101.28 g, namely a dithiocarbamate functionalized dendrimer with a hexanediamine core (HDA/TMPTA/BDA-24CSSNa) with a yield of 93.00%.

A nuclear magnetic resonance $^{13}$C NMR (D$_2$O) spectrum of the obtained star-shaped hyperbranched polymer is: 8.94 ppm, 21.02 ppm, 24.01 ppm, 24.89 ppm, 28.23 ppm, 20.18 ppm, 33.77 ppm, 33.95 ppm, 36.12 ppm, 47.68 ppm, 48.09 ppm, 51.02 ppm, 51.83 ppm, 55.41 ppm, 67.27 ppm, 68.75 ppm, 176.31 ppm, 176.69 ppm, 205.11 ppm and 209.64 ppm. A structure of the HDA/TMPTA/BDA-24CSSNa is:

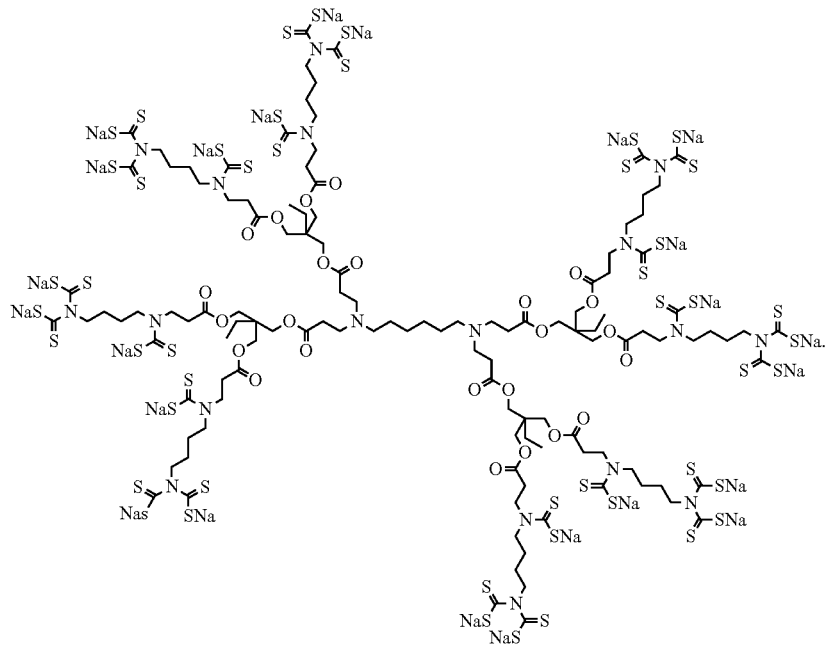

EXAMPLE 3

Application

Tested soil is contaminated by Cd and Pb, and basic physical and chemical properties of the tested soil are showed in Table 1. The dithiocarbamate functionalized dendrimers with the alkylenediamine core as the amendments, obtained by the examples 1 and 2, and the sodium sulfide and the thiourea of the comparisons 1 and 2 were added based on a mass percentage of the soil. Then water, with the same weight as the amendments, was added, and the soil was uniformly mixed. The uniformly mixed soil was dried naturally at a room temperature, so as to obtain immobilized and remedied soil.

TABLE 1

Basic physical and chemical properties of tested soil

| pH | Water content (%) | Plumbum (mg/Kg) | Cadmium (mg/Kg) |
|---|---|---|---|
| 7.37 | 2.03 | 1623.389 | 31.267 |

The soil was tested through an extraction method defined in *Solid waste-Extraction procedure for leaching toxicity-Acetic acid buffer solution* (HJ/T300-2007) to measure a heavy metal content in a leaching liquid. Experimental results are showed in Table 2.

The dithiocarbamate functionalized dendrimer with the alkylenediamine core of the present invention has obviously better immobilization performance for the heavy metals in the soil than conventional amendments, i.e., sodium sulfide and thiourea. For example, when an addition dosage reached 2% of the soil, a leaching value of Cd and Pb of the soil remedied by the amendment of the present invention satisfies concentration requirements of class III, defined in *Quality standard for ground water* (GB/T 14848-93); and, when the addition dosage reached 3% of the soil, the leaching value of Cd and Pb of the soil remedied by the amendment of the present invention satisfies the concentration requirements of class II, defined in the *Quality standard for ground water* (GB/T 14848-93).

When the addition dosage of the thiourea reached 15% of the soil, the leaching value of Cd and Pb of the remedied soil satisfies the concentration requirements of the class IV, defined in *Quality standard for ground water* (GB/T 14848-93).

When the addition dosage of the sodium sulfide reached 15% of the soil, the leaching value of Cd and Pb of the remedied soil is unable to satisfy the concentration requirements of the class IV, defined in *Quality standard for ground water* (GB/T 14848-93).

Thus, compared with the conventional amendments sodium sulfide and thiourea, the dithiocarbamate functionalized dendrimer with the alkylenediamine core of the present invention has highly-efficient immobilization performance for the heavy metals.

TABLE 2

Leaching analysis of heavy metals of immobilized and remedied soil

| Order | Stabilizer | Dosage (%) | Cd leaching concentration (mg/L) | Pb leaching concentration (mg/L) |
|---|---|---|---|---|
| Original soil | — | — | 0.895 | 14.836 |
| Example 1 | BDA/TMPTA/EDA-24CSSNa | 0.5 | 0.238 | 4.236 |
| | | 1.0 | 0.162 | 0.981 |
| | | 2.0 | 0.001 | 0.042 |
| | | 3.0 | 0 | 0.011 |
| Example 2 | HDA/TMPTA/BDA-24CSSNa | 0.5 | 0.227 | 4.192 |
| | | 1.0 | 0.158 | 0.898 |
| | | 2.0 | 0 | 0.034 |
| | | 3.0 | 0 | 0.012 |
| Comparison 1 | sodium sulfide | 3.0 | 0.658 | 11.036 |
| | | 5.0 | 0.515 | 7.357 |
| | | 10.0 | 0.428 | 3.016 |
| | | 15.0 | 0.297 | 1.128 |
| Comparison 2 | thiourea | 3.0 | 0.602 | 8.123 |
| | | 5.0 | 0.359 | 2.108 |
| | | 10.0 | 0.219 | 0.232 |
| | | 15.0 | 0.009 | 0.058 |
| Concentration requirements defined in Quality standard for ground water (GB/T 14848-93) | | Class II | 0.001 | 0.02 |
| | | Class III | 0.01 | 0.05 |
| | | Class IV | 0.01 | 0.1 |

Existing forms of Pb and Cd in the soil were analyzed through a TESSIER method (Tessier A., Campbell P. G. C., Bisson M. *Sequential Extraction Procedure for the Speciation of Particulate Trace Metals* [J]. Analytical Chemistry, 1979, 7(51): 844-850), and experimental results thereof are showed in Table 3 and Table 4.

TABLE 3

Analysis for existing forms of Cd in soil

| | | Existing forms of heavy metals (mg/kg) | | | | | |
|---|---|---|---|---|---|---|---|
| Order | Dosage (%) | Exchangeable | Carbonate bound | Fe—Mn oxidation | Organic bound | Residual | Total |
| Original soil | 0 | 3.233 | 20.230 | 4.675 | 2.087 | 1.042 | 31.267 |
| Example 1 | 0.5 | 0 | 4.598 | 20.529 | 5.652 | 1.128 | 31.907 |
| | 1 | 0 | 2.353 | 12.339 | 15.282 | 2.328 | 32.302 |
| | 2 | 0 | 0 | 11.383 | 19.509 | 3.021 | 33.913 |
| | 3 | 0 | 0 | 6.339 | 17.893 | 6.926 | 31.158 |
| Example 2 | 0.5 | 0 | 4.423 | 21.347 | 5.298 | 1.176 | 32.244 |
| | 1 | 0 | 2.098 | 13.418 | 14.035 | 1.981 | 31.532 |
| | 2 | 0 | 0 | 10.116 | 18.371 | 3.927 | 32.414 |
| | 3 | 0 | 0 | 5.916 | 16.289 | 8.642 | 30.847 |
| Comparison 1 | 3 | 2.086 | 21.615 | 4.455 | 2.161 | 0.942 | 31.259 |
| | 5 | 0.509 | 15.694 | 10.519 | 2.744 | 1.007 | 30.473 |
| | 10 | 0.206 | 10.225 | 17.855 | 3.209 | 1.103 | 32.598 |
| | 15 | 0.358 | 4.627 | 22.117 | 4.172 | 1.011 | 32.285 |

TABLE 3-continued

Analysis for existing forms of Cd in soil

| | | Existing forms of heavy metals (mg/kg) | | | | | |
|---|---|---|---|---|---|---|---|
| Order | Dosage (%) | Exchangeable | Carbonate bound | Fe—Mn oxidation | Organic bound | Residual | Total |
| Comparison 2 | 3 | 0.825 | 19.982 | 5.216 | 1.985 | 1.079 | 29.087 |
| | 5 | 0.012 | 17.237 | 9.015 | 2.689 | 1.102 | 30.044 |
| | 10 | 0 | 7.248 | 18.896 | 4.009 | 1.282 | 31.435 |
| | 15 | 0 | 2.001 | 23.349 | 5.937 | 1.198 | 32.485 |

TABLE 4

Analysis for existing forms of Pb in soil

| | | Existing forms of heavy metals (mg/kg) | | | | | |
|---|---|---|---|---|---|---|---|
| Order | Dosage (%) | Exchangeable | Carbonate bound | Fe—Mn oxidation | Organic bound | Residual | Total |
| Original soil | 0 | 57.883 | 806.545 | 420.158 | 302.406 | 36.397 | 1623.389 |
| Example 1 | 0.5 | 3.092 | 559.469 | 452.638 | 541.625 | 97.681 | 1654.505 |
| | 1 | 0 | 213.328 | 467.822 | 782.261 | 165.223 | 1628.634 |
| | 2 | 0 | 79.813 | 377.562 | 819.711 | 344.948 | 1622.034 |
| | 3 | 0 | 11.252 | 263.699 | 787.538 | 624.972 | 1687.461 |
| Example 2 | 0.5 | 3.298 | 556.669 | 450.183 | 592.242 | 73.284 | 1675.676 |
| | 1 | 0 | 228.902 | 476.198 | 773.923 | 145.232 | 1624.255 |
| | 2 | 0 | 81.292 | 369.155 | 820.119 | 354.458 | 1624.024 |
| | 3 | 0 | 11.252 | 263.699 | 787.518 | 664.872 | 1727.341 |
| Comparison 1 | 3 | 40.921 | 822.834 | 449.039 | 304.495 | 36.839 | 1654.128 |
| | 5 | 22.297 | 834.626 | 424.905 | 310.395 | 35.396 | 1627.619 |
| | 10 | 7.296 | 682.277 | 580.592 | 312.881 | 42.315 | 1625.361 |
| | 15 | 2.895 | 372.669 | 796.723 | 478.099 | 52.676 | 1673.062 |
| Comparison 2 | 3 | 23.043 | 839.486 | 423.672 | 301.153 | 37.388 | 1624.742 |
| | 5 | 8.223 | 777.747 | 487.879 | 372.359 | 46.025 | 1692.233 |
| | 10 | 1.098 | 327.664 | 784.136 | 475.915 | 57.023 | 1645.836 |
| | 15 | 0 | 117.808 | 953.943 | 498.517 | 57.142 | 1627.41 |

According to the Table 3, when the addition dosage of the amendment of the present invention reached 0.5% of the soil (illustrated with the example 1), the exchangeable forms of Cd were completely immobilized; the carbonate bound forms of Cd were decreased from 20.230 mg/Kg to 4.598 mg/Kg; the Fe—Mn oxidation and the organic bound forms of Cd were respectively increased from 4.675 mg/Kg and 2.087 mg/Kg to 20.529 mg/Kg and 5.652 mg/Kg; and the residual forms of Cd were stable. That is to say, the exchangeable and a portion of the carbonate bound forms of Cd were changed into the more stable Fe—Mn oxidation and organic bound forms of Cd. When the addition dosage of the amendment of the present invention reached 2% of the soil, the exchangeable and the carbonated bound forms of Cd were completely immobilized; and, the Fe—Mn oxidation, the organic bound and the residual forms of Cd were all increased. That is to say, all of the exchangeable and the carbonated bound forms of Cd were changed into the more stable Fe—Mn oxidation, organic bound and residual forms of Cd. The sodium sulfide was merely able to partially decrease the exchangeable and carbonate bound forms of Cd ions; and when the addition dosage of the thiourea reached 10% of the soil, the exchangeable and a portion of the carbonated bound forms of the Cd ions were decreased.

According to the Table 4, when the addition dosage of the amendment of the present invention reached 1% of the soil (illustrated with the example 1), the exchangeable forms of Pb were completely immobilized; the carbonate bound forms of Pb were decreased from 806.545 mg/Kg to 213.328 mg/Kg; the Fe—Mn oxidation, the organic bound and the residual forms of Pb were all slightly increased. That is to say, the exchangeable and a portion of the carbonated bound forms of Pb were changed into the more stable Fe—Mn oxidation, organic bound and residual forms of Pb. When the addition dosage of the amendment of the present invention reached 3% of the soil, the carbonate bound forms of Pb were decreased to 5.259 mg/Kg; and the Fe—Mn oxidation forms of Pb were decreased from 420.158 mg/Kg to 263.669 mg/Kg. That is to say, all of the exchangeable, 99.34% of the carbonated bound and 37.25% of the Fe—Mn oxidation forms of Pb were changed into the more stable organic bound and residual forms of Pb. The sodium sulfide was merely able to partially decrease the exchangeable and the carbonate bound forms of Pb ions; and when the addition dosage of the thiourea reached 15% of the soil, the exchangeable and a portion of the carbonate bound forms of the Pb ions were decreased.

Bio-availability of the heavy metals in the soil is closely related to chemical forms of the heavy metals. The exchangeable forms of heavy metal ions, which plants are able to directly absorb and utilize, belong to direct available forms of the heavy metal ions (available forms of the heavy metal ions). The carbonate bound, the Fe—Mn oxidation, the organic bound and the residual forms of the heavy metal ions need to be changed into the exchangeable forms of the heavy metal irons respectively under an acidic condition, a deoxidization condition, an oxidation condition and a strong oxidation condition, before being absorbed by the plants. It is almost impossible for the soil in a natural world to be exposed to the deoxidization environment, the oxidation environment and the strong oxidation environment, but possible for the soil in the natural world to be exposed to an acid rain environment. Thus, the carbonate bound forms of the heavy metal irons are able to be changed into the exchangeable forms of the heavy metal ions under the acid rain and thus belong to potential exchangeable forms of the heavy metal ions.

The dithiocarbamate functionalized dendrimer with the alkylenediamine core, provided by the present invention, is able to effectively immobilize the exchangeable forms of Cd and Pb and the carbonated bound forms of Cd and Pb, with a low addition dosage, to avoid a possibility that the heavy metals of the remedied soil are dissolved out again under the acid rain condition and guarantee a long-term safety of the soil.

What is claimed is:

1. A dithiocarbamate functionalized dendrimer with an alkylenediamine core as a soil heavy metal immobilization amendment, wherein:

the dithiocarbamate functionalized dendrimer with the alkylenediamine core has a chemical formula of:

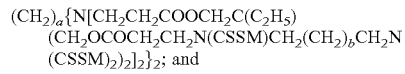
$(CH_2)_a\{N[CH_2CH_2COOCH_2C(C_2H_5)(CH_2OCOCH_2CH_2N(CSSM)CH_2(CH_2)_bCH_2N(CSSM)_2)_2]_2\}_2$; and the dithiocarbamate functionalized with the alkylenediamine core has a chemical formula of:

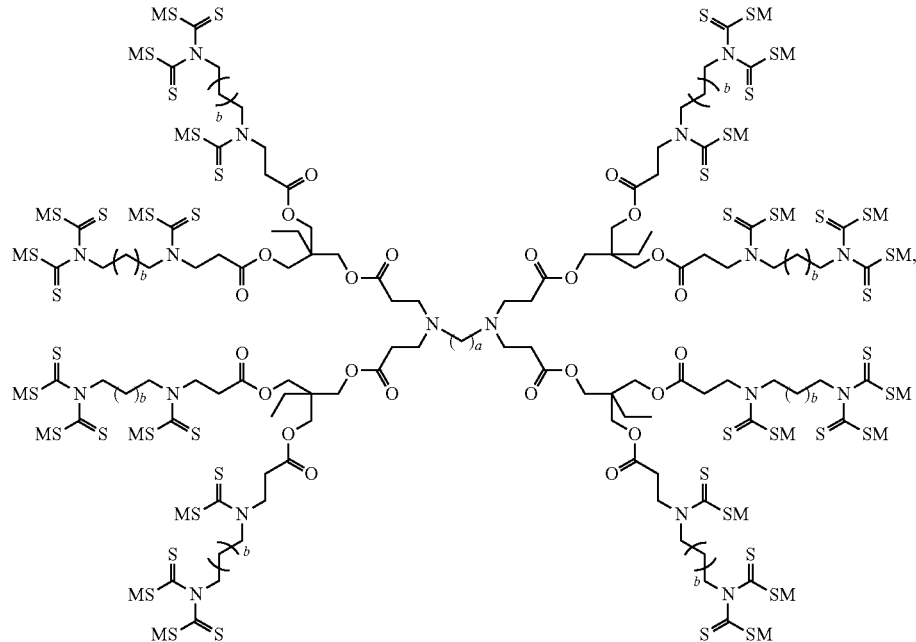

wherein a is a positive integer larger than 2, b is a positive integer at a range of 0-4, and M is $Na^+$, $NH_4^+$ or $K^+$.

* * * * *